United States Patent [19]

Peers-Trevarton

[11] 4,437,474
[45] Mar. 20, 1984

[54] METHOD FOR MAKING MULTICONDUCTOR COIL AND THE COIL MADE THEREBY

[75] Inventor: Charles A. Peers-Trevarton, Coral Springs, Fla.

[73] Assignee: Cordis Corporation, Miami, Fla.

[21] Appl. No.: 399,063

[22] Filed: Jul. 16, 1982

[51] Int. Cl.³ .............................................. A61N 1/04
[52] U.S. Cl. ................................ 128/784; 128/419 P; 128/780; 29/605; 29/618; 29/876; 29/872
[58] Field of Search ..................... 128/419 P, 784, 785, 128/786; 174/103, 105 R; 29/876, 605, 618, 882, 879, 872, 868

[56] References Cited

U.S. PATENT DOCUMENTS

| | | | |
|---|---|---|---|
| 3,572,344 | 3/1971 | Boldue | 128/786 |
| 3,596,662 | 8/1971 | Boldue | 128/786 |
| 4,236,525 | 12/1980 | Slvetz et al. | 128/419 P |
| 4,394,866 | 7/1983 | Hughes | 128/419 P X |
| 4,402,330 | 9/1983 | Lindemans | 128/786 |

Primary Examiner—Edward M. Coven
Attorney, Agent, or Firm—Henry W. Collins; Thomas R. Vigil

[57] ABSTRACT

The method of the present invention is used to make a multiconductor coil having an outer diameter equal to the diameter of a winding mandrel plus the diameter of wires being coiled while preserving homogeneity of the insulating coating and of the insulation between the wires. The method includes the steps of: winding a first uninsulated wire conductor on a winding mandrel with a predetermined spacing between adjacent turns of the coil of wire conductor; coating the uninsulated coil of wire conductor with an insulating coating; repeating the above two steps for each additional wire conductor to be included in the multiconductor coil; and, after the insulating coating on each wire conductor coil has dried and/or solidified, screwing each additional coil into the first coil to form a multiconductor coil having a desired homogeneity of the insulating coating and of the insulation between adjacent turns in the multiconductor coil.

5 Claims, 9 Drawing Figures

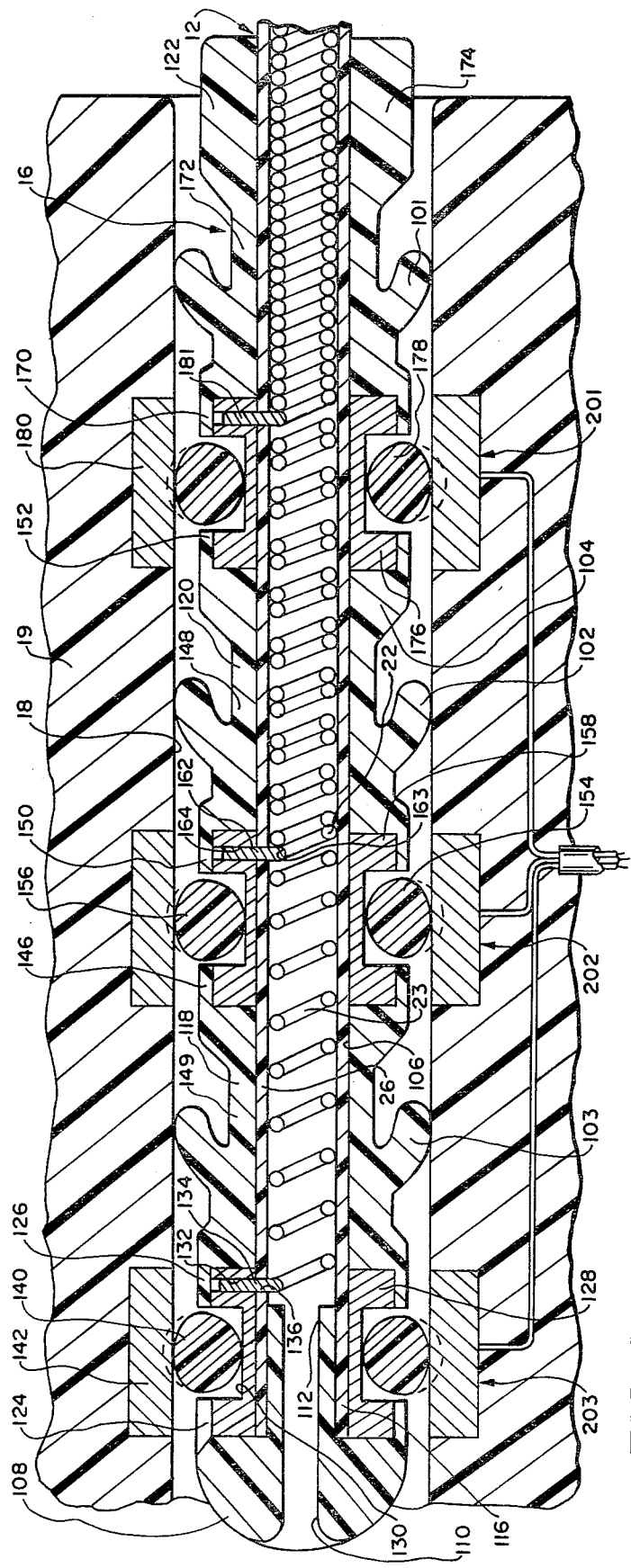

METHOD FOR MAKING MULTICONDUCTOR COIL AND THE COIL MADE THEREBY

BACKGROUND OF THE INVENTION

1. Field of the Invention

The present invention relates to multiconductor, multifilar coils utilized in a pacing lead assembly.

2. Description of the Prior Art

Heretofore multifilar, single conductor coiled pacing leads have been utilized in pacing lead assemblies having a multipolar electrode assembly at the distal end thereof and a connector at the proximal end thereof for connecting the conductor lead to a pulse generator. An example of such a bipolar lead assembly is disclosed in U.S. Pat. No. 4,236,525 which discloses a lead assembly for a body implantable tissue stimulator having two distal electrodes and proximal connectors that are coaxially and axially spaced for mating with corresponding stimulator output electrodes in a pulse generator.

The connectors heretofore utilized for connecting the proximal end of a multifilar conductor pacing lead to a pulse generator such as the connectors disclosed in U.S. Pat. No. 4,236,525 have worked satisfactorily. However, due to recent developments in cardiac pacing technology, leads having multiple conductors but of the same diameter or a small diameter than unipolar and bipolar leads are necessary.

The insert connector at the proximal end of the pacing lead of the present invention solves this problem by providing one or more spool-shaped metal bands about the proximal end of the pacing lead and connected to individual wire conductors of the lead with an elastic conductive ring positioned about the spool adapted to contact a metal sleeve or ring embedded in the side wall of a socket in a body portion of the pulse generator into which the insert connector is inserted.

Also as will be described in greater detail hereinafter, the multipolar electrode assembly at the distal end of the multiconductor pacing lead of the present invention is constructed in such a way as to facilitate solid electrical contact between the ends of each wire conductor in the multiconductor lead and individual electrodes of the electrode assembly and in such a way as to take up a minimum of space thereby to enable a very compact minimum diameter electrode assembly to be provided.

In the forming of a multiconductor lead, a plurality, such as three, insulated wire conductors are wound on a wire mandrel so as to form a multi-conductor coiled lead having the outside diameter of only one coil, i.e., the diameter of the winding mandrel plus twice the diameter of the insulated coated wire. However, this technique for making such a minimum diameter multiconductor coil has not provided a coil wherein the insulating coating is homogenous throughout the multiconductor coil. In this respect, due to the tension which has to be applied to the coated wires in attempting to wind them on the winding mandrel, the wire may act like a "cheese cutter" and cut through the part of the insulating coating which is between the wire and the winding mandrel. When this happens, the inside surfaces of the coiled wires are no longer insulated, the enclosing envelope of insulation around the wires is no longer intact and the insulating materials can part company from the wire allowing them to touch and short circuit. Also, a short circuit could be formed when a wire stylet is inserted within the enclosing envelope and makes contact with the exposed wires.

An example of the prior art technique for winding one or more insulated wire conductors on a mandrel is disclosed in U.S. Pat. No. 3,572,344.

As will be disclosed in greater detail hereinafter, the method of the present invention eliminates this problem of breaks in the insulating coating by forming the individual wire coils that are to be combined in a multiwire conductor coil in an uninsulated form on a winding mandrel. Then, the uninsulated wire conductor coils thus formed are coated with an insulating material and the coated wire conductor coils are screwed into one another thereby to form a multiconductor coil.

SUMMARY OF THE INVENTION

According to the invention there is provided a method for making a multiconductor coil having an outer diameter equal to the diameter of a winding mandrel plus the diameter of wires being coiled with homogeneity of the insulating coating and the insulation between the wires preserved, said method comprising the steps of: winding a first uninsulated wire conductor on a winding mandrel with a predetermined spacing between adjacent turns of the coil of wire conductor, coating the uninsulated coil of wire conductor with an insulating coating, repeating the above two steps for each additional wire conductor to be included in the multiconductor coil, and after the insulating coating on each wire conductor coil has dried and/or solidified, screwing each additional coil into the first coil to form a multiconductor coil having the desired homogeneity of the insulating coating and of the insulation between adjacent turns in the multiconductor coil.

BRIEF DESCRIPTION OF THE DRAWINGS

FIG. 3 is an enlarged sectional view of the multipolar insert connector at the proximal end of the pacing lead assembly shown in FIG. 1 received in a socket in a body portion of the pulse generator shown in FIG. 1.

FIG. 4 is a fragmentary view partially in section showing the prior art manner of winding a multifilar, multiconductor coil on a mandrel.

FIG. 5 is a cross section of a single filar coil wound according to the teachings of the present invention and shows the spacing dimension between spaced apart turns of the single filar coil.

DESCRIPTION OF THE PREFERRED EMBODIMENTS

Figure 1:
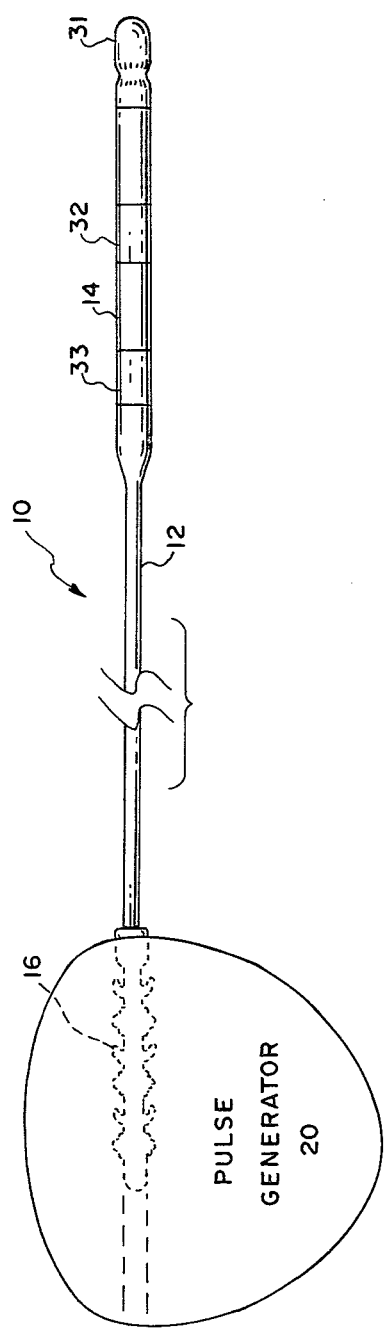
FIG. 1 is a side view of a pulse generator and pacing lead assembly which are constructed in accordance with the teachings of the present invention.

Referring now to FIG. 1 there is illustrated therein a pulse generator and pacing lead assembly 10 which includes a multifilar pacing lead 12 having at its distal end a multipolar electrode assembly 14 and a multipolar insert connector 16 at the proximal end thereof which is received within a socket 18 (FIG. 3) formed in a body portion 19 (FIG. 3) in a pulse generator 20.

Figure 2:
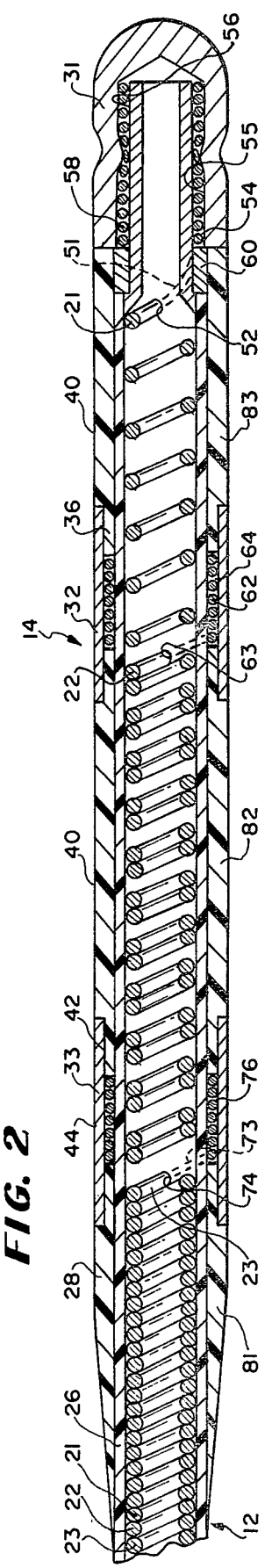
FIG. 2 is an enlarged sectional view of a multipolar electrode tip assembly which is mounted at the distal end of the pacing lead assembly shown in FIG. 1.

Referring now to FIG. 2 there is illustrated therein a cross section of the multifilar pacing lead 12 and of the multipolar electrode assembly 14. As shown, the multifilar pacing lead 12 includes three filars or wires 21, 22 and 23 which are wound in a single coil in accordance with the teachings of the present invention as will be described in greater detail hereinafter in connection with the description of FIGS. 4–9.

The coiled filars 21, 22 and 23 are surrounded by an insulating sheath 26 which can be made of silicone, polyurethane, or other insulating material, but preferably is formed of PARYLENE "C" manufactured by Union Carbide Corporation.

The distal end of the pacing lead 12 extends within an electrode body 28 made of an insulating material and which forms part of the multipolar electrode assembly 14. Mounted at the distal end of the body 28 is a first electrode 31 which can be referred to as a tip electrode 31. Then, spaced from the tip electrode 31 is a second sleeve electrode 32 and a third sleeve electrode 33 is spaced from the second sleeve electrode 32. The sleeve electrode 32 is received in an annular slot 36 formed in the body 28 so that outer facing surface 38 of the sleeve electrode 32 is flush with outer cylindrical surface 40 of the insulating body 28. Likwise, the second sleeve electrode 33 is an annular slot 42 in the insulating body 28 so that outer surface 44 thereof is flush with the cylindrical surface 40 of the insulating body 28.

Although not illustrated in FIG. 2, it is to be understood that each of the filars or wires 21–23 has an insulating coating thereon so that it is insulated from the adjacent filar.

As shown in FIG. 2, the first filar 21 extends all the way to the first tip electrode 31 and an end portion 51 of the first filar 21 extends through an opening 52 in the sheath 26. This end portion 51 is stripped of insulation and extends from the opening 52 in the sheath 26 through a slot (not shown) in the sheath 26 to an annular cavity 54 defined between an inner cylindrical surface 55 formed within the electrode 31 and outer surface 56 of a plug 58 which extends from the inner end of the sheath 26 around a ring 60 and into the cylindrical cavity 55. The electrode 31 is crimped at several points to retain the first filar 21 between the outer surface 56 of the plug 58 and the inner cylindrical surface 55 of electrode 31 thereby to ensure a good electrical connection therewith.

In a similar manner, an end portion 62 of the second filar or wire 22 is stripped of insulation so as to be a bare wire and extends through an opening 63 in the sheath 26 through a passageway in the sheath 26 to an annular passageway 64 where the bare filar end portion 62 is coiled. The annular passageway 64 is defined between a thin layer (not shown) of electrode body 28 or the outer surface of the sheath 26 and the inner surface of the sleeve electrode 32. The width or thickness of the annular passageway 64 is such that the bare wire end portion 62 is urged against the inner surface of the sleeve electrode 32 thereby to ensure a good electrical contact therewith.

Further, and in like manner, the third filar 23 has a bare end portion 73 which extends through an opening 74 in the sheath 26 and through a slot in the sheath 26 to an annular passageway 76 between a thin layer of the electrode body 28 or the outer surface of the sheath 26 and the inner surface of the third sleeve electrode 33. Also, the dimension or width of the annular passageway 76 is such that the bare filar end portion 73 wound in a coil in the annular passageway 76 is urged against the inner surface of the sleeve electrode 33.

It will be appreciated from the foregoing description that the insulating body 28 which surrounds the distal end of the pacing lead 12 has been defined as one piece construction but is shown in FIG. 2 as being of three piece construction, namely of three elements 81, 82 and 83.

The multipolar electrode assembly 14, and in this particular instance, a three polar assembly 14, enables a physician to select any one of the three electrode 31, 32 or 33 for pacing the myocardium and for using any one of the electrodes 31, 32 and 33 for relaying information about selected tissue back to the pulse generator 20.

In FIG. 3 is illustrated the position of the insert connector 16 at the proximal end of the multifilar pacing lead 12 received in the socket 18 in the body portion 19 of the pulse generator 20. As shown, the sidewall of the socket 18 is adapted to receive resilient flanges 101, 102 and 103 which extend from and are integral with an insulating body portion 104 of the insert connector 16. As shown in FIG. 3, when the insert connector 16 is inserted into the socket 18, the flanges 101, 102 and 103 will be flexed as shown for sealing the insert connector 16. Typically, the insulator body 104 and the flanges 101, 102 and 103 extending therefrom are made from an elastomeric insulating material such as silicone. The sealing arrangement shown in FIG. 3 is of the type shown in U.S. Pat. No. 4,259,962.

As shown in FIG. 3, the insulator body 104 has a central passageway 106 therein which is sized to receive the proximal end of the multifilar pacing lead 12. The end 108 of the insulator body 104 of the insert connector 16 has a central passageway 110 therethrough which extends into the insulator body 104 and through a cylindrical protrusion 112 about which the proximal end 116 of the sheat 26 is received. This passageway 110 permits a stylet to be inserted through the passageway 110 and the insulator body 104 into the coiled filars 21, 22 and 23 within the sheath 26 of the multifilar pacing lead 12.

Although the insulator body 104 has been described above as being of unitary construction, it is preferably, and as shown in FIG. 3, made of insulating body segments which include the end segment 108, two identical intermediate segments 118 and 120 and an outer end segment 122. The end segment 108 has an outer annular flange 124 extending inwardly and axially of the insert connector 16 and is spaced radially outwardly from the cylindrical protrusion 112.

The intermediate segment 118 has a similar annular flange 126 which extends toward the annular flange 124 so as to define an annular space, open in the middle, between the outer surface of the sheath 26 and the annular flanges 124 and 126. Received within this annular space is a spool-shaped metal band or ring 128 which has an annular slot 130 therein. The spool-shaped metal band 128 has a radial slot 132 therein which receives the bare end 134 of the filar 23 which bare end 134 extends from the insulated filar 23 through an opening 136 in the sheath 26.

Received within the slot 130 in the spool-shaped metal band 128 is a resilient ring 140 of conductive material which is adapted to electrically contact the slot 130 on its inwardly facing side and to electrically contact a metal ring 142 embedded in the body 19 and having an inwardly facing surface flush with the surface of the socket 18.

The conductive ring 140 is preferably made of a conductive resilient material such as silicon rubber. Also, as shown in FIG. 3, the ring 140 has a diameter which is greater than the space between the outer surface of the spool-shaped metal band 128 and the metal ring 142 embedded in the body 19 and having an inner surface flush with the surface of the socket 18 so that the ring 140 will be squeezed when the insert connector 16 is inserted into the socket 18. This is brought out in FIG. 3 by the showing of the normal unsqueezed position of the ring in phantom in FIG. 3.

It is to be understood that the conductive ring 140 can also be made of other materials. For example, it could be a so-called garter spring which is a coiled spring in which two ends are brought together and welded so as to form a toroid envelope which can be squeezed when the insert connector 16 is inserted into the socket 18.

Another type of conductive ring would be a ring made of woven metal. In this respect, a flat sheet of woven metal could be rolled into a roll and then the roll formed into a toroid with the ends welded together, thereby to form a resilient ring 140. As is apparent, there are numerous other conductive materials and configurations thereof which could be utilized to form the conductive ring 140.

The insulator segment 118 in addition to having the radially extending annular flange 103 and the axially extending annular flange 126 has a reduced-in-diameter portion 144 for facilitating flexing of the flange 103 when the insert connector 16 is inserted into the socket 18. Further, the segment 118 has another axially extending annular flange 146 as shown.

The insulator segment 120 is identical to the insulator segment 118 and in addition to having a radially extending flange 102, it has a reduced-in-diameter portion 148 and annular flanges 150 and 152. The insulator segment 120 is positioned on the sheath 26 such that the annular flanges 150 and 146 form with the outer surface of the sheath 26 an annular space, open in the middle, for receiving a conductive resilient ring 154 which makes contact with a metal ring 156 embedded in the side wall of the socket 18 in the body portion 19 and the exposed surface of a spool-shaped metal band 158 received in the annular space. A bare end 162 of filar 22 extends through an opening 163 in the sheath 26 and is received in a slot 164 in the spool-shaped metal band 158 for making electrical contact therewith. In this way as in the previous electrical connection described above, electrical contact is effected between the end 162 of the filar 22 through the metal band 158 and resilient conductive ring 154 to metal ring 156.

The insulator segment 122 is similar in construction to insulator segments 118 and 120 by having an axially extending annular flange 170 at one end thereof, the radially extending flange 101 and a reduced-in-diameter section 172. The outer end of segment 122 is a solid body 174, as shown, which is received about the multifilar pacing lead 12.

The opposed ends of the insulator segments 120 and 122 form an annular space for receiving a spool-shaped metal band 176 which has a conductive ring 178 extending thereabout and adapted to make electrical contact with a metal ring 180 embedded in the side wall of the socket 18 as shown. Also, a bare end 181 of filar 21 extends through the sheath 26 where it is rigidly fixed into a slot in the spool-shaped metal band 176 to ensure a good electrical contact therewith.

It will be understood that the radially extending flanges 101, 102 and 103 can be sized and configured to sealingly fit against the side wall of the socket 18.

With the construction of the insert connector 16 and the socket 18 as described above, three electrical connector assemblies, 201, 203 and 204 are created for facilitating good electrical connection between the ends 134, 162 and 181 of the filars 23, 22 and 21 to the pulse generator circuitry (not shown) within the pulse generator 20.

Heretofore in constructing the multifilar pacing lead 12 a plurality of, e.g., three, filars 21, 22 and 23 are wound in a group on a mandrel 210 as shown in FIG. 4. As brought out in FIG. 4, the filars 21, 22 and 23 are already coated with an insulating material 221, 222 and 223. One of the problems incurred in preparing the multifilar coil comprised of three filars 21, 22 and 23 by winding them on a mandrel to form the coil which is received within the sheath 26 of the pacing lead 12 is that the pressure exerted on the wire as it is wound tight on the mandrel causes the wires or filars 21–23 to cut through the insulating coating material 221–223 in a "cheese cutting" manner. As a result, breaks in the insulation are incurred and when a metal stylet is inserted within the multifilar coil, shorting can occur between the stainless steel wire stylet and the exposed filars.

This problem is overcome by the method of the present invention which, simply stated, comprises the steps of first winding each coil separately, second coating each coil thus formed with insulating material, and third screwing the two or more, and in this case three, coils together to form the multifilar coil. In this way, a multifilar, multiconductor coiled pacing lead is obtained having the outside diameter of only one coil which has the diameter of a winding mandrel plus twice the diameter of the insulated coated filars or wires. At the same time, breaking of the insulated coating which has heretofore been caused by the tension which had to be applied to the coated wires in attempting to wind them on a winding mandrel is avoided.

In accordance with the teachings of the present invention and as illustrated in FIG. 5, a filar is wound in such a manner that when it is coated with an insulant or insulating material, there will be a certain spacing X between adjacent turns of the coil. In this respect, the formula used for determining the spacing X is as follows:

$$X = [(n-1)d] + (n\,g)$$

where
  n = desired number of filars,
  d = diameter of wire and insulant, and
  g = gap required between adjacent filars in the multifilar coil (if any).

For a three filar coil where the outer diameter of the filar and insulant coating is 0.005 inch and the gap is 0.0005 inch $$x=[(3-1)0.005]+(3\ 0.0005)$$

$$x=0.0115$$

Figure 6:
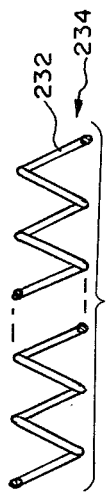
FIG. 6 is a fragmentary view of one filar coil wound according to the teachings of the present invention prior to being insulated.

With reference to FIGS. 5 and 6, a bare or uninsulated filar or wire 232, in accordance with the method of the present invention, is wound on a mandrel to form the bare coil 234 shown in FIG. 6 and having the spacing requirements shown in FIG. 5 after it has been coated with a layer of insulant or insulating material 236. In constructing a three conductor or filar multifilar lead where the thickness of the bare wire is 0.003 inch in diameter and the insulating coating is 0.001 inch thick and a gap of 0.005 inch is desired, applying the formula for x set forth above, x=0.0115 inch.

Accordingly, the filar or wire 232 is wound on a mandrel having a spacing of x+0.002 (the thickness of the insulant 216) which equals 0.0135 inch between adjacent turns of the coil 234 of uninsulated filar 232.

Figure 7:
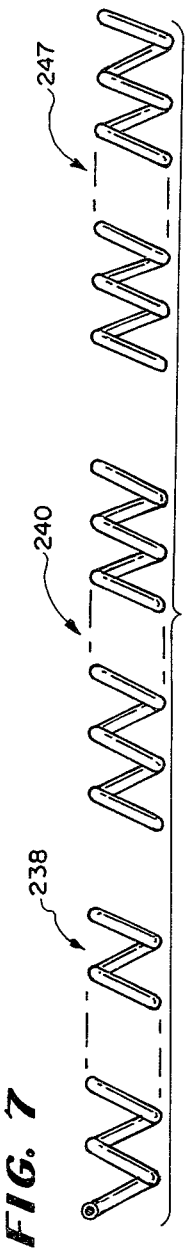
FIG. 7 is a fragmentary exploded view of three filar coils after they have been wound and insulated according to the teachings of the present invention.

The coil 234 is then coated with an insulating material such as by fluidized bed coating, dip coating, spray coating, vacuum coating, vapor deposition coating, or any of a multiplicity of means for coating bare wire with an insulating material, and then allowed to dry or solidify to form a first insulated filar coil 238 shown in FIG. 7. Then, repeating the steps described above, two more insulated filar coils 240 and 242 are prepared.

Figure 8:
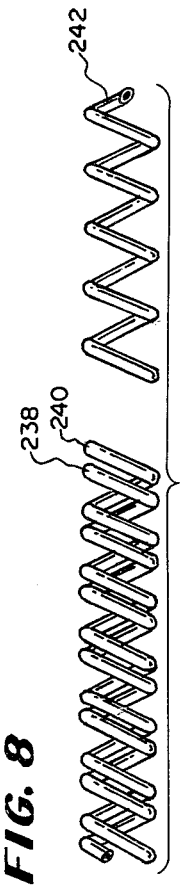
FIG. 8 is an exploded fragmentary view similar to FIG. 7 and shows one filar coil screwed into another filar coil with the third filar coil yet to be screwed into the first two filar coils to create a multifilar coil.
Figure 9:
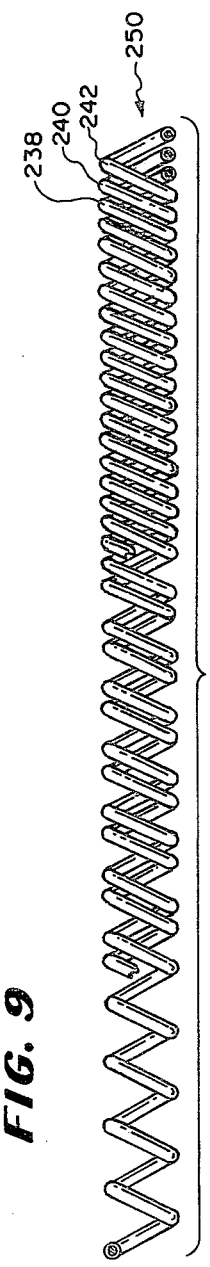
FIG. 9 is a view similar to FIG. 8 but showing all the filar coils screwed together at one end of the multifilar coil and with one filar coil extending the length of the multifilar coil shown, a second filar coil extending two thirds the length of the multifilar coil shown and a third filar coil extending one third the length of the multifilar coil shown.

Next, the coil 240 is screwed into the coil 238 as shown in FIG. 8. Then, the third coil 242 is screwed into the already screwed together coils 240 and 238 to form a multiconductor, multifilar coil 250 for insertion within a sheath 26 to form the pacing lead 12.

In this way, a tri-filar coiled lead 12 is obtained having three conducting wires or filars 21, 22 and 23 insulated and without there being any breaks in the insulation or insulant coating, facing the inner cylindrical envelope formed by the tri-filar coil 250. In this way the homogeneity of the insulating coating and of the insulation between the wires or filars is preserved.

It will be understood that although the method of the present invention has been particularly described with reference to three wires or filars, any number of wires, e.g., two or more, can be wound into a multifilar coil utilizing the method of the present invention.

From the foregoing description it will be apparent that the pulse generator and pacing lead assembly of the present invention and specifically the multifilar coil 250 made according to the method of the present invention for the multifilar pacing 12 have a number of advantages, some of which have been described above and others of which are inherent in the invention. Also it will be apparent to those skilled in the art that modifications can be made to the method and multifilar coil of the present invention without departing from the teachings of the present invention. Accordingly, the scope of the invention is only to be limited as necessitated by the accompanying claims.

I claim:

1. A method for making a multiconductor coil having an outer diameter equal to the diameter of a winding mandrel plus the diameter of wires being coiled with homogeneity of the insulating coating and the insulation between the wires peserved, said method comprising the steps of: winding a first uninsulated wire conductor on a winding mandrel with a predetermined spacing between adjacent turns of the coil of wire conductor, coating the uninsulated coil of wire conductor with an insulating coating, repeating the above two steps for each additional wire conductor to be included in the multiconductor coil, and after the insulating coating on each wire conductor coil has dried and/or solidified, screwing each additional coil into the first coil to form a multiconductor coil having the desired homogeneity of the insulating coating and of the insulation between adjacent turns in the multiconductor coil.

2. The method according to claim 1 wherein the predetermined spacing is determined by the following formula:

$$x=[(n-1)d]+(n\ g)$$

where
 x=the desired spacing,
 n=the desired number of wire conductors,
 d=diameter of wire conductor and insulating coating, and
 g=the gap required (if any) between adjacent turns in the multiconductor coil.

3. The method according to claim 1 wherein the multiconductor coil includes three wire conductors.

4. A multiconductor coil made by the method of claim 1.

5. A pacing lead assembly including a pacing lead comprising a multiconductor coil made by the method of claim 1 and an outer sheath surrounding the multiconductor coil.

* * * * *